(12) United States Patent
Park et al.

(10) Patent No.: US 7,906,358 B2
(45) Date of Patent: Mar. 15, 2011

(54) EPITAXIAL GROWTH OF CUBIC CRYSTALLINE SEMICONDUCTOR ALLOYS ON BASAL PLANE OF TRIGONAL OR HEXAGONAL CRYSTAL

(75) Inventors: Yeonjoon Park, Yorktown, VA (US);
Sang H. Choi, Poquoson, VA (US);
Glen C. King, Yorktown, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 12/254,017

(22) Filed: Oct. 20, 2008

(65) Prior Publication Data

US 2009/0140296 A1 Jun. 4, 2009

Related U.S. Application Data

(60) Provisional application No. 60/980,880, filed on Oct. 18, 2007, provisional application No. 60/980,878, filed on Oct. 18, 2007, provisional application No. 60/980,881, filed on Oct. 18, 2007, provisional application No. 60/980,871, filed on Oct. 18, 2007, provisional application No. 60/980,870, filed on Oct. 18, 2007, provisional application No. 60/980,876, filed on Oct. 18, 2007.

(51) Int. Cl.
*H01L 21/00* (2006.01)
*H01L 29/22* (2006.01)
*H01L 29/20* (2006.01)
*H01L 21/02* (2006.01)

(52) U.S. Cl. ............ 438/47; 438/46; 257/614; 257/615; 257/616

(58) Field of Classification Search ...................... 438/47
See application file for complete search history.

(56) References Cited

U.S. PATENT DOCUMENTS

| 5,394,826 | A | 3/1995 | Ebe et al. |
| 6,096,389 | A | 8/2000 | Kanai |
| 7,247,885 | B2 * | 7/2007 | Rankin et al. .................. 257/87 |
| 2006/0163612 | A1 | 7/2006 | Kouvetakis et al. |
| 2007/0069195 | A1 | 3/2007 | Park et al. |
| 2007/0222034 | A1 * | 9/2007 | Park et al. ..................... 257/616 |

OTHER PUBLICATIONS

Chaldyshev et al. In "Zinc blende GaAs films grown on wurtzite GaN/sapphire templates", Mar. 23, 2005, Applied Physics Lette, vol. 86, 131916.*
Park et al. in "Comparison of zinc-blende and wurtzite GaN semiconductors with spontaneous polarization and piezoelectric field effects", Sep. 23, 1999, Journal of Applied Physics, vol. 87(1), 353-364.*

* cited by examiner

*Primary Examiner* — N Drew Richards
*Assistant Examiner* — Michael Jung
(74) *Attorney, Agent, or Firm* — Thomas K. McBride; Robin W. Edwards (57) ABSTRACT

Hetero-epitaxial semiconductor materials comprising cubic crystalline semiconductor alloys grown on the basal plane of trigonal and hexagonal substrates, in which misfit dislocations are reduced by approximate lattice matching of the cubic crystal structure to underlying trigonal or hexagonal substrate structure, enabling the development of alloyed semiconductor layers of greater thickness, resulting in a new class of semiconductor materials and corresponding devices, including improved hetero-bipolar and high-electron mobility transistors, and high-mobility thermoelectric devices.

5 Claims, 10 Drawing Sheets

$a'' = \frac{2a}{\sqrt{3}}$

Lattice constant relationship in Type [B] alignment

Two types of possible crystal structure alignment on trigonal crystal substrate Type [A] and Type [B]

EPITAXIAL GROWTH OF CUBIC CRYSTALLINE SEMICONDUCTOR ALLOYS ON BASAL PLANE OF TRIGONAL OR HEXAGONAL CRYSTAL

CROSS-REFERENCE TO RELATED APPLICATIONS

This application claims the benefit of the respective filing dates of the following commonly assigned U.S. Provisional Patent Application Ser. No. 60/980,870 filed on Oct. 18, 2007, Ser. No. 60/980,871 filed on Oct. 18, 2007, Ser. No. 60/980,878 filed on Oct. 18, 2007, Ser. No. 60/980,880 filed on Oct. 18, 2007, and Ser. No. 60/980,881 filed on Oct. 18, 2007, each of which contains an overlap of inventive entity with the present application. In addition, this application incorporates by reference the entire disclosures of the following commonly assigned nonprovisional U.S. patent applications being filed on the same date as the present application Ser. No. 12/254,016, entitled "THERMOELECTRIC MATERIALS AND DEVICES;" Ser. No. 12/254,134, entitled "HYBRID BANDGAP ENGINEERING FOR SUPER-HETERO-EPITAXIAL SEMICONDUCTOR MATERIALS, AND PRODUCTS THEREOF;" Ser. No. 12/288,379, entitled "RHOMBOHEDRAL CUBIC SEMICONDUCTOR MATERIALS ON TRIGONAL SUBSTRATE WITH SINGLE CRYSTAL PROPERTIES AND DEVICES BASED ON SUCH MATERIALS;" Ser. No. 12/288,380, entitled "X-RAY DIFFRACTION WAFER MAPPING METHOD FOR RHOMBOHEDRAL SUPER-HETERO-EPITAXY;" and Ser. No. 12/254,150, entitled "METHOD OF GENERATING X-RAY DIFFRACTION DATA FOR INTEGRAL DETECTION OF TWIN DEFECTS IN SUPER-HETERO-EPITAXIAL MATERIALS;" each one claiming priority to the above cited provisional applications.

ORIGIN OF THE INVENTION

This invention was made in part by employees of the United States Government and may be manufactured and used by or for the Government of the United States of America for governmental purposes without the payment of any royalties thereon or therefor.

BACKGROUND OF THE INVENTION

1. Field of the Invention

The present invention is in the fields of solid-state physics, semiconductor material and heteroepitaxy, and more particularly concerns lattice-matching methods for rhombohedral growth of crystals comprised of semiconductor alloys of group IV and other cubic crystalline materials on the basal plane of trigonal or hexagonal crystalline substrates, and the resulting semiconductor compositions.

2. Description of the Related Art

The alloys of group IV elements, including carbon (C), silicon (Si), germanium (Ge), and tin (Sn) are important semiconductor materials. For example, SiGe alloy is widely used in Hetero Bipolar Transistors (HBT) and High Electron Mobility Transistors (HEMT) for high speed computing and wireless communications, as well as in Thermoelectric (TE) materials. The growth of these alloys has been very difficult because the alloy has a different lattice constant from that of the commonly used substrate, such as Si wafer. Prior efforts have tried to match the lattice constant of cubic structures directly, such as by the approach wherein $L_{target}=L_{substrate}$ (the lattice constant of cubic substrate). However, even a small mismatch of these parameters can result in extremely high pressures in the alloy layer. Thus, in prior efforts, the thickness of the grown layers was very small and often had a high density of defects such as misfit dislocations.

Similar considerations apply with respect to other cubic crystalline semiconductor materials, including group III-V and II-VI materials in zinc-blende structure, as well as other materials in Body Centered Cubic (BCC) and Face Centered Cubic (FCC) structures.

SUMMARY OF THE INVENTION

It is an object of the present invention to develop new methods for controlling the growth of rhombohedral crystals composed of group IV alloys and other cubic crystalline materials on trigonal and/or hexagonal crystal substrates, and thereby to provide new and useful alloyed semiconductor materials which previously could not be reliably produced.

Accordingly, the present invention provides heteroepitaxial semiconductor materials comprising rhombohedral crystals of group IV semiconductor alloys and other cubic crystalline materials grown on the basal plane of trigonal and hexagonal substrates in which misfit dislocations are reduced by lattice matching of the overlying rhombohedral to underlying trigonal or hexagonal substrate structure. This enables the development of alloyed group IV and other cubic crystalline semiconductor layers of greater thickness, resulting in a new class of semiconductor materials and corresponding devices, including improved heterobipolar and high-electron mobility transistors, and high-mobility thermoelectric devices.

To achieve these results, the present invention generally uses a new lattice matching technique to calculate alloy compositions in order to approximately match substrate lattices, and thereby allow the growth of group IV alloy and other cubic crystal layers that are much more free of dislocation defects than those that could be obtained under prior approaches. The present approach relates to any alloys of silicon (Si), germanium (Ge), carbon (C) and tin (Sn) (generally referred to in this specification as "SiGeCSn") on any trigonal/hexagonal substrate, such as sapphire (i.e. single crystalline $Al_2O_3$) (or hexagonal substrates, such as quartz), as well as to other cubic crystalline materials, including group III-V and II-VI materials in zinc-blende structure, and potentially to other materials in Body Centered Cubic (BCC) and Face Centered Cubic (FCC) structures.

In one embodiment, lattice matching equations, when satisfied by a particular alloy composition, will result in good crystal growth of the alloy on rhombohedral, trigonal, or hexagonal substrates. Further, techniques for calculating Bragg angles and inter-planar angles for twin detection for all group IV alloys as well as group III-V and II-VI materials in zinc-blende structure, on any trigonal or hexagonal substrate, may be applied to a new X-ray diffraction method for twin detection developed in accompanying patent application Ser. No. 12/254,150, entitled "METHOD OF GENERATING X-RAY DIFFRACTION DATA FOR INTEGRAL DETECTION OF TWIN DEFECTS IN SUPER-HETERO-EPITAXIAL MATERIALS," and Ser. No. 12/288,380, entitled "X-RAY DIFFRACTION WAFER MAPPING METHOD FOR RHOMBOHEDRAL SUPER-HETERO-EPITAXY;" which have both been incorporated herein by reference (specific XRD methods are claimed in the separate applications).

The present invention makes it possible, for example, to incorporate a high content of germanium and tin atoms into silicon without critical thickness limit because it is lattice-matched, thereby providing an increase in the built-in electric field for faster SiGeCSn HBT and HEMT devices and more efficient SiGeCSn TE devices than previously possible. Other aspects and advantages of the present invention will be apparent from the accompanying drawings, and the detailed description that follows.

BRIEF DESCRIPTION OF THE DRAWINGS

For a more complete understanding of the present invention and the advantages thereof, reference is now made to the following description taken in conjunction with the accompanying drawings, wherein like reference numerals represent like parts, in which:

FIG. 1 graphically depicts in FIG. 1 (a) the primitive unit cell of trigonal crystal structure of sapphire ($Al_2O_3$) and FIG. 1 (b) the diamond structure of Si, Ge, C and Sn.

FIG. 4 shows the direction of SiGe [220] in FIG. 4 (a) real-lattice and sapphire [1-104], in FIG. 4 (b) reciprocal lattice and in FIG. 4 (c) real-space lattice. All arrows are projected on the basal plane.

DETAILED DESCRIPTION

The following is a detailed description of certain embodiments of the invention chosen to provide illustrative examples of how it may preferably be implemented. The scope of the invention is not limited to the specific embodiments described, nor is it limited by any specific implementation, composition, embodiment or characterization depicted in the accompanying tables or drawings or stated or described in the invention summary or the abstract. In addition, it should be noted that this disclosure describes a number of methods that each comprise a plurality of steps. Nothing contained in this written description should be understood to imply any necessary order of steps in such methods, other than as specified by express claim language.

In the ensuing description, the well-known Miller indices notation of lattice planes is used. That is, crystal planes are designated by numbers within "( )", groups of similar planes are designated by numbers within "{ }", direction or length is designated by numbers within "[ ]", and groups of similar directions are designated by numbers within "< >".

Figure 1A:
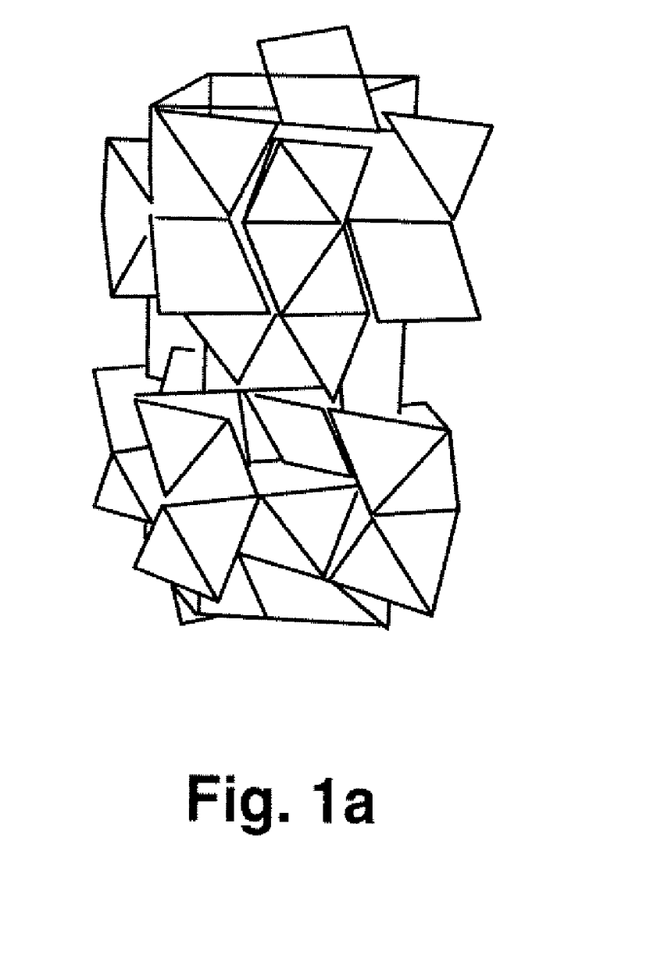
Figure 1B:
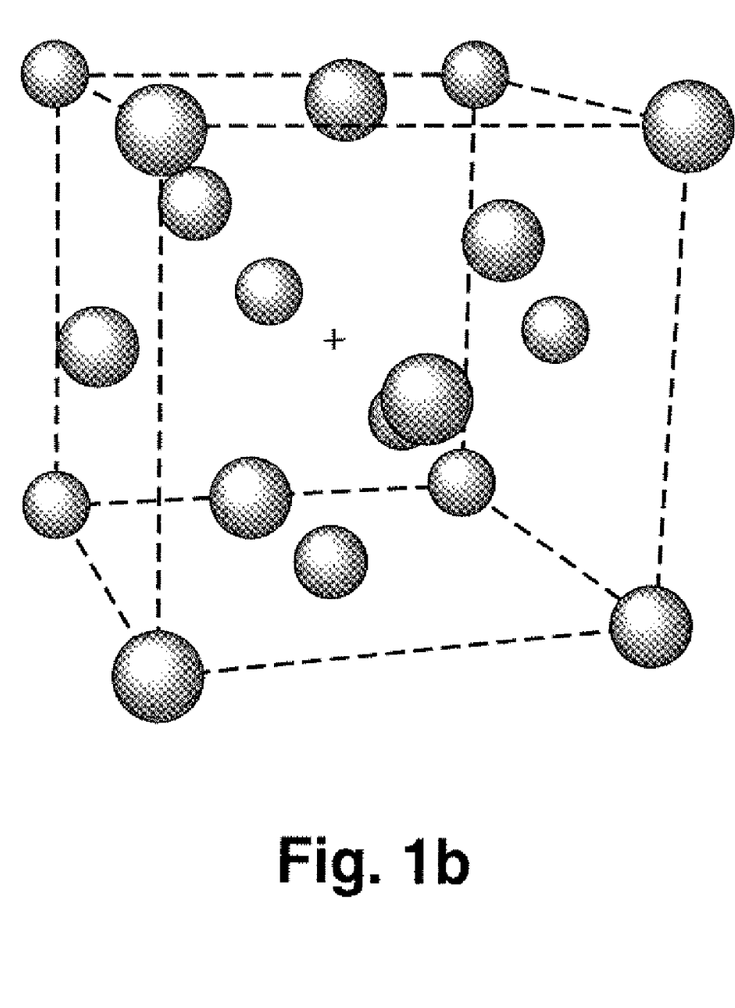
Figure 2:
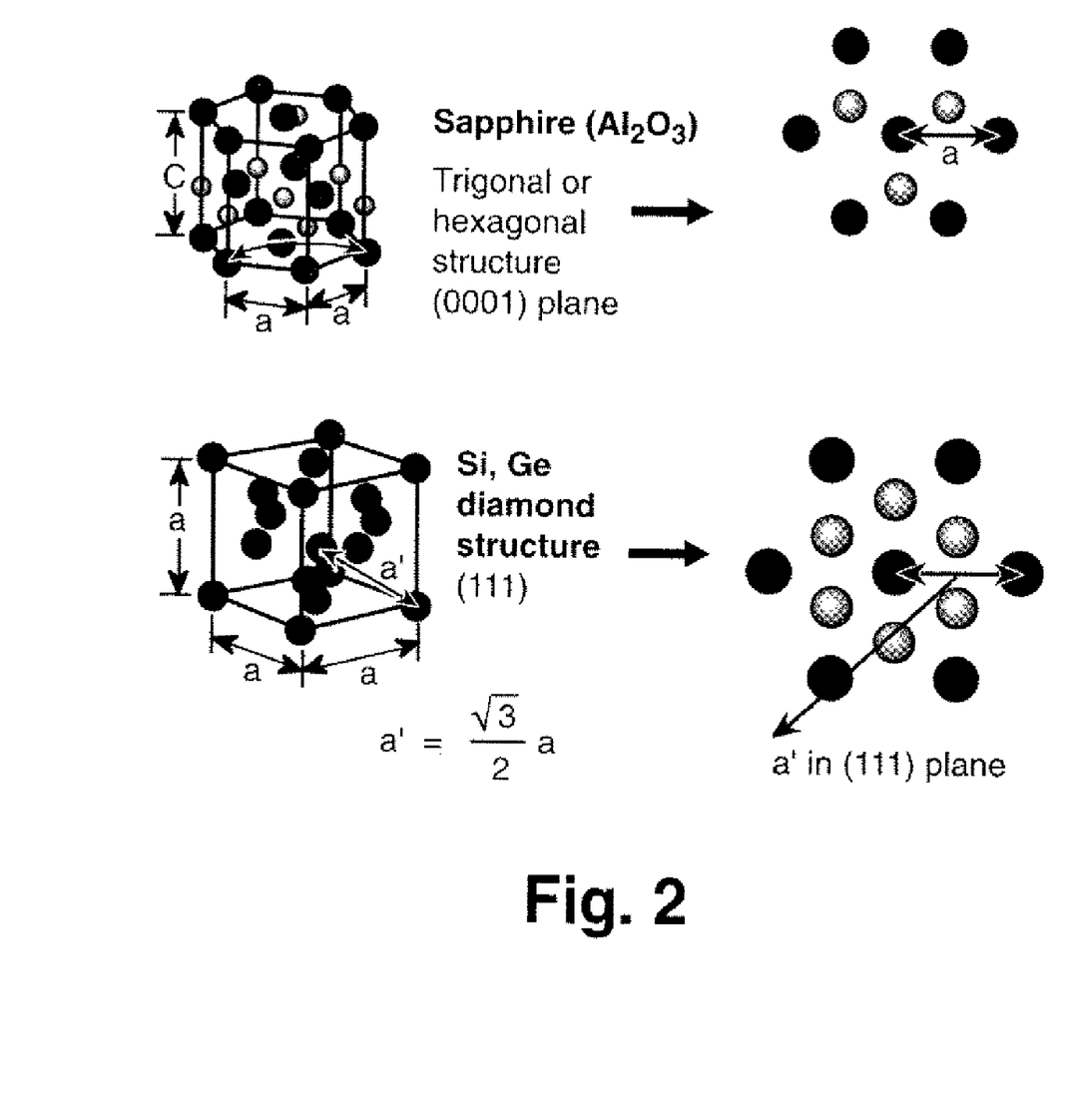
FIG. 2 shows the crystal lattice constant relationship between rhombohedral transformation of diamond cubic structure and simplified crystal structure of sapphire. The actual crystal structure of sapphire is very complex and not shown here.

Sapphire has a trigonal crystal structure as shown in FIG. 1 (a). The group IV elements, Si, Ge, C, and Sn, have cubic diamond structures as shown in FIG. 1 (b) (and group III-V and II-VI crystalline materials in zinc-blende configuration have a similar crystal structure). Therefore, the direct comparison of lattice constants does not have a meaning since the cubic basal plane, i.e. {001} planes according to Miller index classification, cannot be aligned on the trigonal basal plane, i.e. the {0001} or "C" plane. However, if we consider a rhombohedral transformation of cubic crystals along the <111> direction, we can see that trigonal {111} planes of cubic crystals can match the trigonal {0001} planes easily, as shown in FIG. 2. In this case, a new lattice parameter of cubic crystal, shown as a' in FIG. 2, can match the corresponding lattice parameter, a, of the underlying trigonal or hexagonal crystalline substrate. Here, the [220] atomic distance a' is given by the rhombohedral transformation relation:

$$a'_{cubic} = \frac{\sqrt{3}}{2} a_{cubic} \tag{1}$$

"Type [A]" alignment is used for the above atomic arrangement at the interface of epitaxial material and substrate material.

Figure 3:
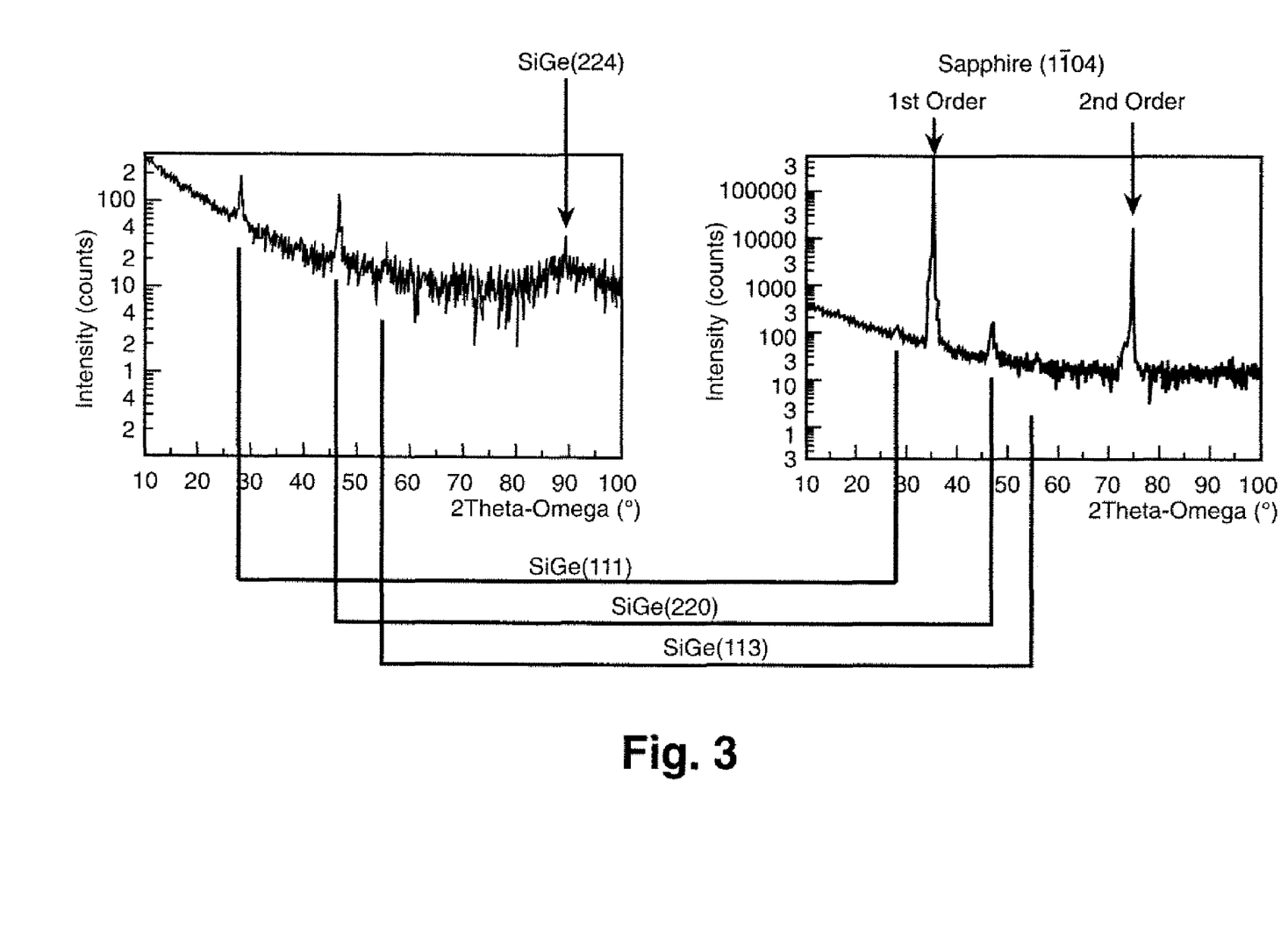
FIG. 3 shows plots of two kinds of X-ray diffraction data which were obtained at different Euler angles (the two sets of data were obtained at Phi angles which were apart by 60°).
Figure 4A:
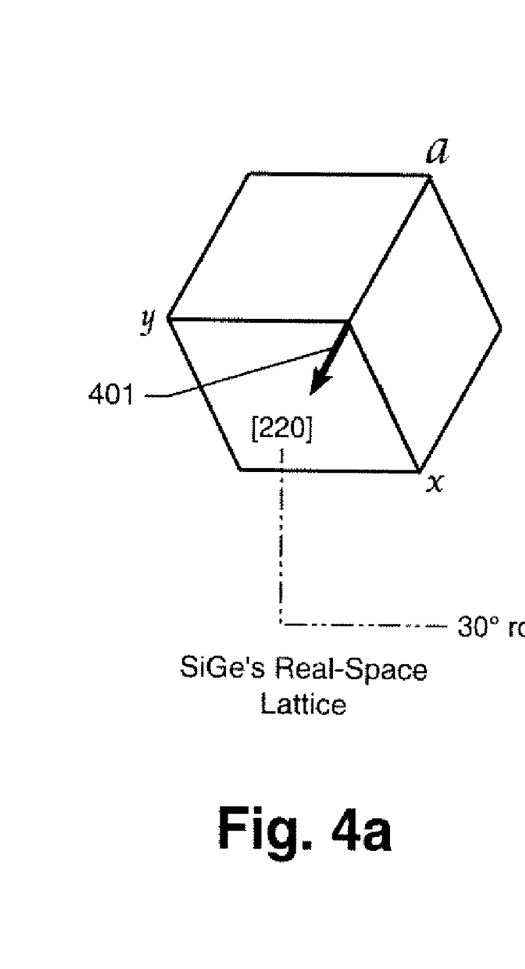
Figure 4B:
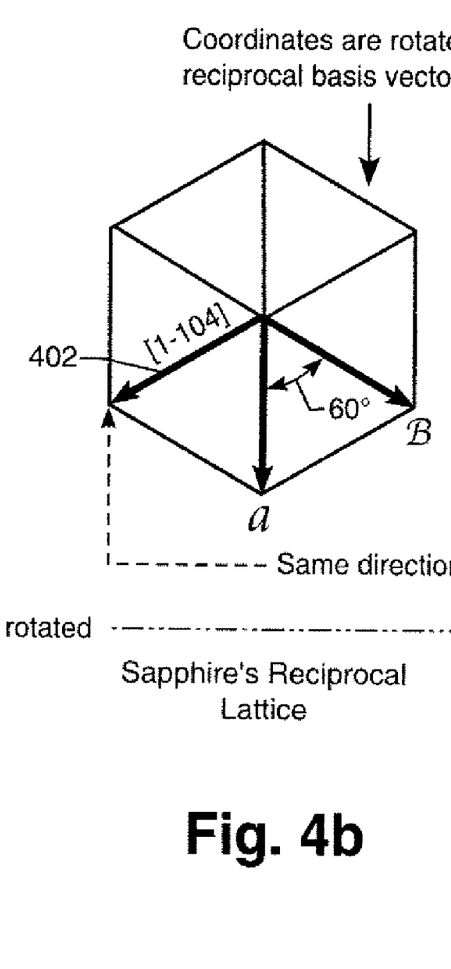
Figure 4C:
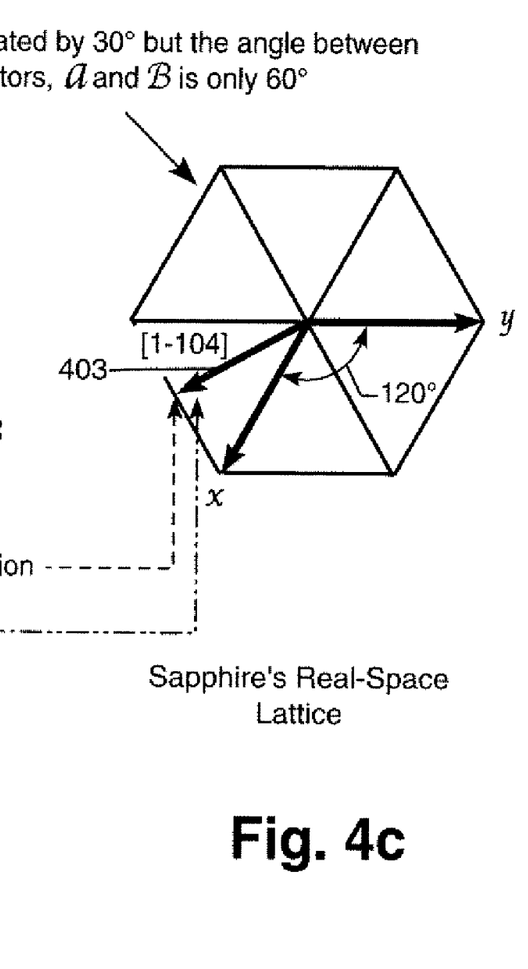
Figure 5:
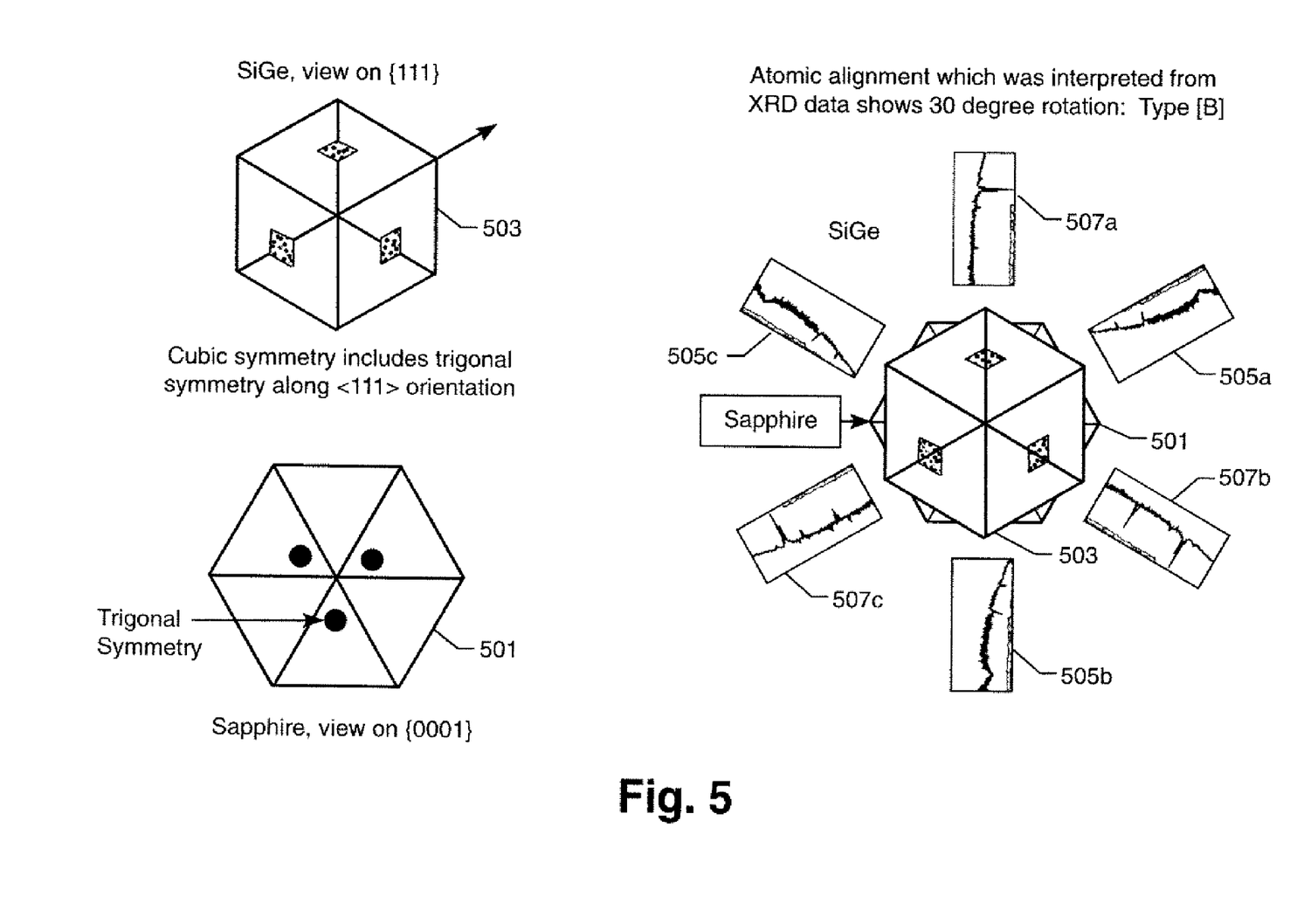
FIG. 5 shows atomic alignment of SiGe on sapphire, in a Type [B] alignment.

XRD methods are used to confirm the present crystal growth methodology and the resulting materials. FIG. 3 shows two sets of X-ray diffraction data (angle-dependent single crystalline XRD) of one SiGe layer on sapphire substrate which was grown at a certain growth condition. Two sets of data were obtained at the same 2-Theta (detector), Omega (goniometer), Chi (tilt) angles, but at different Phi angles, which were apart by 60°. In this tilted XRD data, (111), (113), (220), and (224) peaks were obtained in θ-2θ scan, which means that poly-crystalline SiGe films were formed on sapphire under a certain growth condition. It is important to notice that the first and the second order peaks of sapphire (1-104) were obtained in the second set of data, but there is no sapphire (1-104) peak in the first set of data. The lack of (1-104) peak in the first set of data shows the trigonal symmetry of sapphire substrate such that 60° rotational symmetry is broken and only 120° rotational symmetry is valid in sapphire. The (220) peak in the first set of data shows one domain and another (220) peak in the second set of data shows the other domain, which was aligned with sapphire's (1-104). The coexistence of SiGe's (220) peak and sapphire's (1-104) peak in one single θ-2θ scan shows a different new atomic alignment scheme, as shown in FIG. 4 and FIG. 5.

In a non-cubic crystal system, the reciprocal lattice orientation can be different from the real space lattice orientation. In a trigonal/hexagonal system, the reciprocal basis vectors (shown as α and β in FIG. 4 (b)) have 30° rotation from real-space lattice vectors (shown as x and y in FIG. 4 (c)) but the angle between the reciprocal basis vectors, α and β is not 120°, but only 60° according to the definition equation below. On the other hand, the cubic system's reciprocal basis vectors are the same as real space basis vectors. Therefore, extra-care must be paid to the crystal plane orientation between the cubic system and the trigonal/hexagonal system because of the transformation of the basis vectors. The vector transformation relation is given in the following equation (See N. W. Ashcroft, N. D. Mermin, Solid State Physics, in Chapter 5 "The Reciprocal Lattice", Harcourt College Publishers, New York, ISBN#0-03-083993-9 (1976)):

$$\vec{b}_1 = 2\pi \frac{\vec{a}_2 \times \vec{a}_3}{\vec{a}_1 \cdot (\vec{a}_2 \times \vec{a}_3)}, \tag{2}$$

$$\vec{b}_2 = 2\pi \frac{\vec{a}_3 \times \vec{a}_1}{\vec{a}_1 \cdot (\vec{a}_2 \times \vec{a}_3)},$$

-continued $$\bar{b}_3 = 2\pi \frac{\bar{a}_1 \times \bar{a}_2}{\bar{a}_1 \cdot (\bar{a}_2 \times \bar{a}_3)}$$

where $\bar{a}_1, \bar{a}_2$, and $\bar{a}_3$ are the basis vectors of real-space and $\bar{b}_1, \bar{b}_2$, and $\bar{b}_3$ are the basis vectors of reciprocal space.

In FIG. 4, a1, and a2 are shown as x and y, b1 and b2 are shown as α and β. The comparison of crystal orientations between cubic and cubic, or between trigonal/hexagonal and trigonal/hexagonal systems do not have this problem. By contrast, the comparison of crystal orientations between cubic and trigonal/hexagonal systems must consider the rotation and inter-vector-angle change of lattice basis vectors in reciprocal space of the trigonal/hexagonal crystal. Because the line 401 in FIG. 4 (a) and line 403 in FIG. 4 (c) have to be aligned in the same direction for two peaks to appear in the same θ-2θ XRD scan, the SiGe crystal is atomically aligned to sapphire's hexagonal basal plane as shown in FIG. 5, which shows 30° rotation.

In FIG. 5, sapphire substrate is shown as hexagon 501 with three dots that represent trigonal symmetry, and SiGe epitaxial layer is shown as superimposed hexagon 503 with three tiny parallelograms that is aligned with 30° rotation with respect to hexagon 501. Six angle-dependent single crystalline XRD data sets are shown in the corresponding azimuthal orientation in Euler angles. These six XRD data sets are categorized in two groups (505a-c and 507a-c) having similar nature respectively, indicating trigonal symmetry. Therefore, all the drawings and data in FIG. 5 show that the grown epitaxy layer is atomically aligned according to a new atomic alignment lattice-matching scheme, which is characterized by 30° rotation between the projected lattice axis of epitaxial layer and substrate layer. This additional atomic alignment will be referred to as "Type [B]" alignment.

Figure 6:
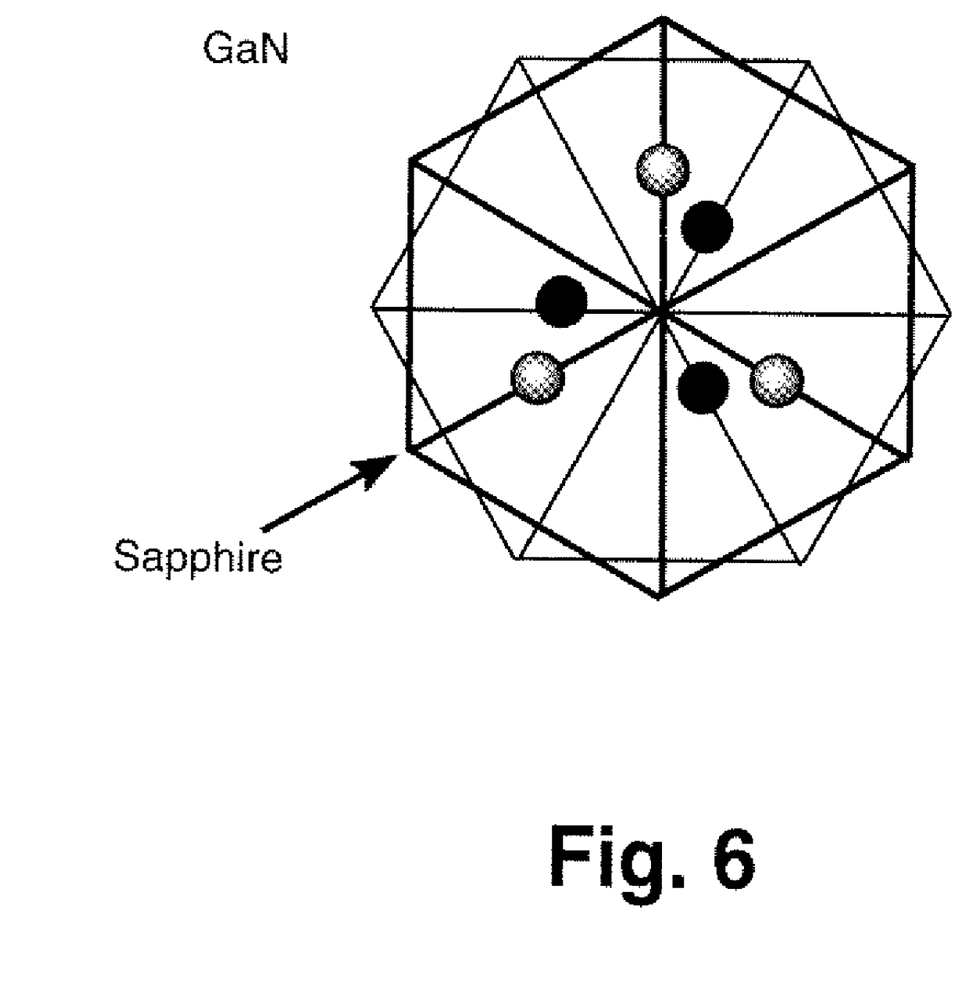
FIG. 6 shows 30° rotated atomic alignment of GaN on sapphire, in a Type [B] alignment.

Some other material systems also show this kind of atomic alignment, which is identified by 30° rotation of rhombohedral epitaxial layer on trigonal (or hexagonal) substrate. For example, it has been reported previously that gallium nitride (GaN) on sapphire has 30° rotation between GaN epitaxial layer and sapphire substrate as shown in FIG. 6. (See Yamaguchi T, Araki T, Santo Y, et al, Journal of Crystal Growth 237: 993-997 Part 2 (2002), Akasaka T, Kobayashi Y, Ando S, Kobayashi N, App. Phys. Lett. 71 (15): 2196-2198 (1997), H. M. Manasevit, F. M. Erdmann, and W. I. Simpson, J. Electrochem. Soc. 118, 1864 (1971), and T. Sasaki and S. Zembutsu, J. Appl. Phys. 61, 2533 (1987).)

Figure 7:
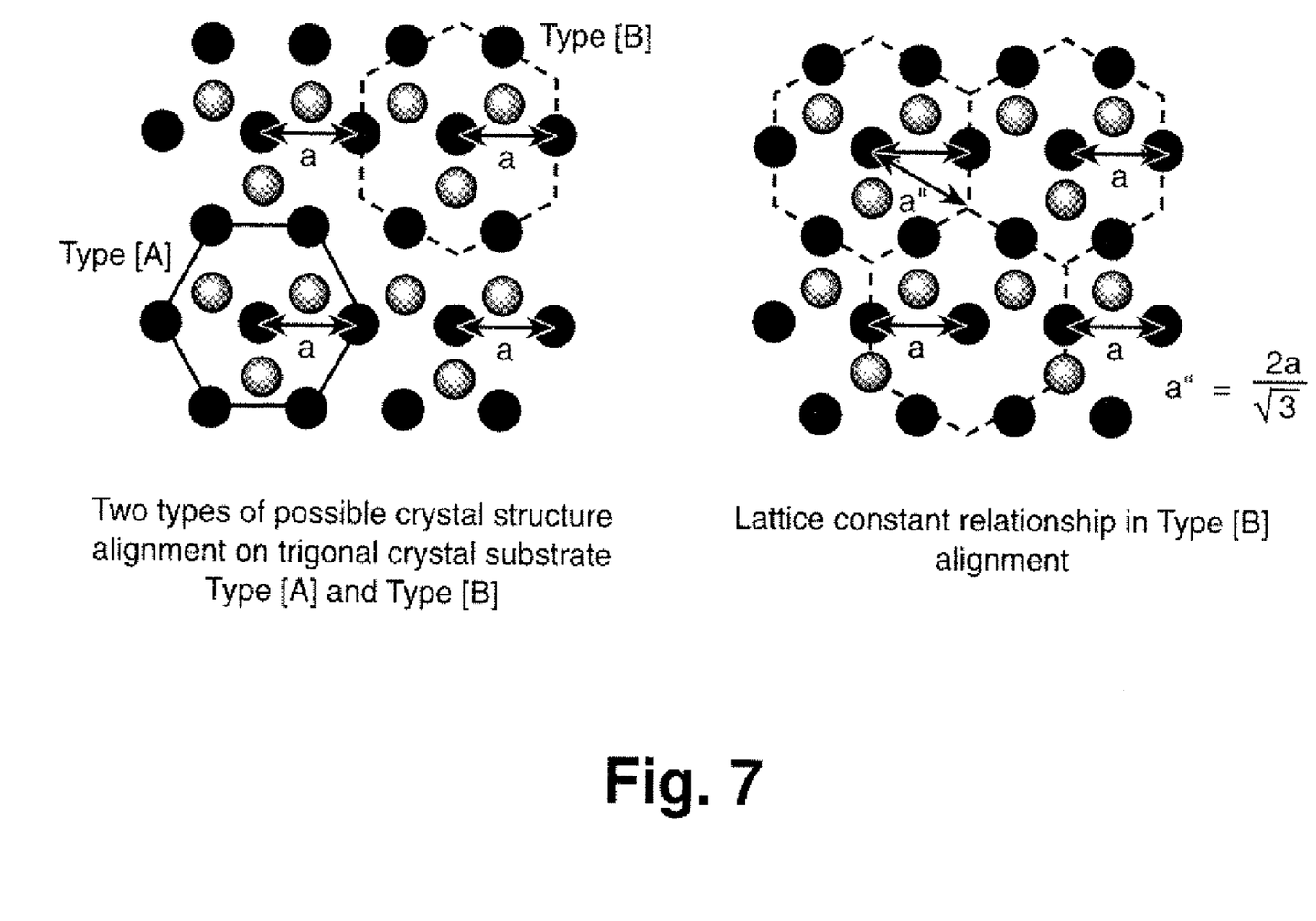
FIG. 7 shows a comparison between Type [A] and Type [B] atomic alignment, with different lattice matching conditions.

Both atomic alignment configurations, Type [A] and Type [B], have to be considered in order to expand the lattice matching methods for various group IV alloys and group III-V and group II-VI crystalline materials in zinc-blende structure on many different trigonal or hexagonal substrates. FIG. 7 shows the lattice matching conditions in Type [A] alignment and Type [B] alignment (See also FIG. 2 with regard to Type [A]). The lattice matching conditions are different for Type [A] and Type [B]. See equations (13)-(16) below.)

Figure 8:
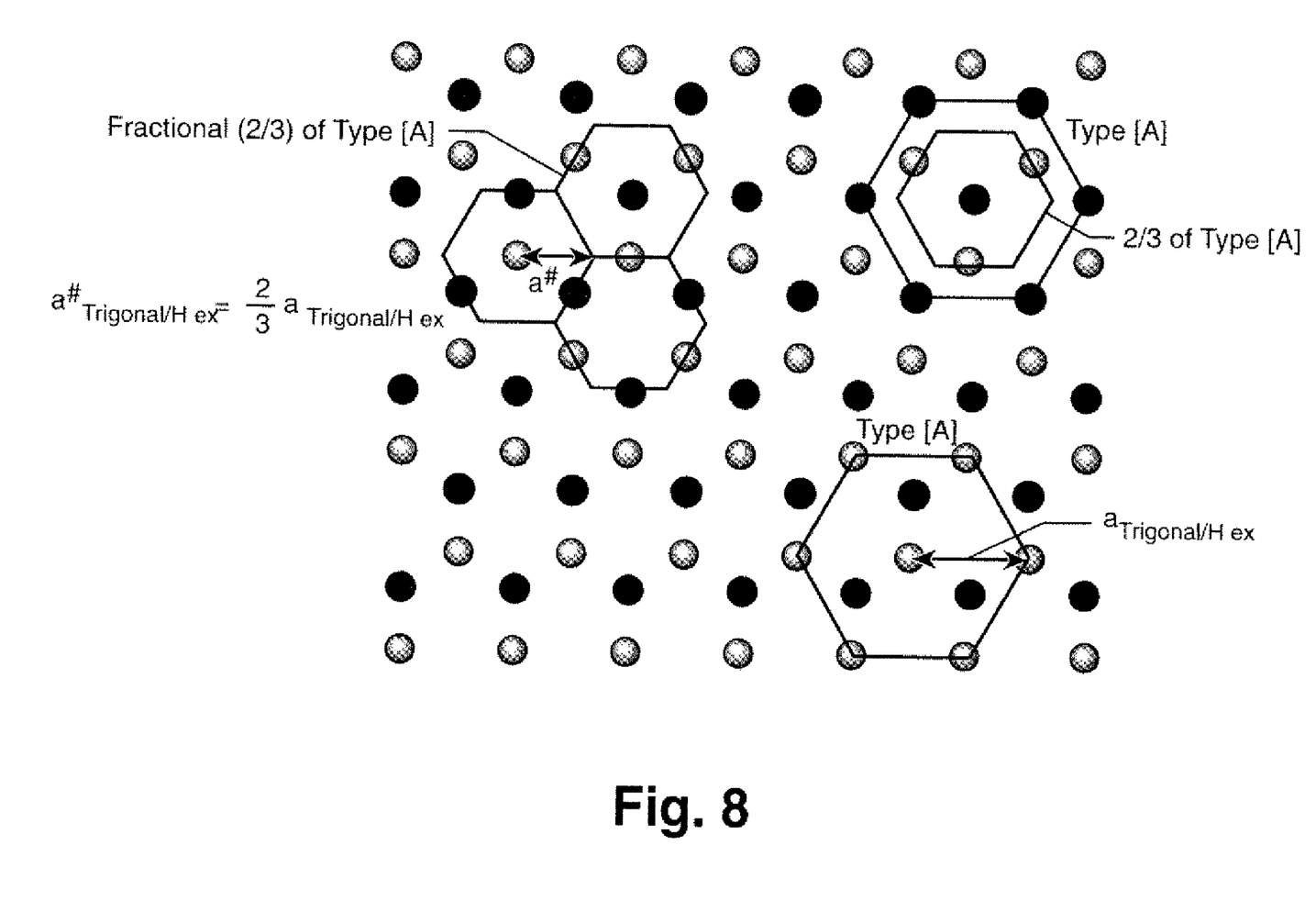
FIG. 8 shows fractional "⅔ of Type [A] alignment."
Figure 9:
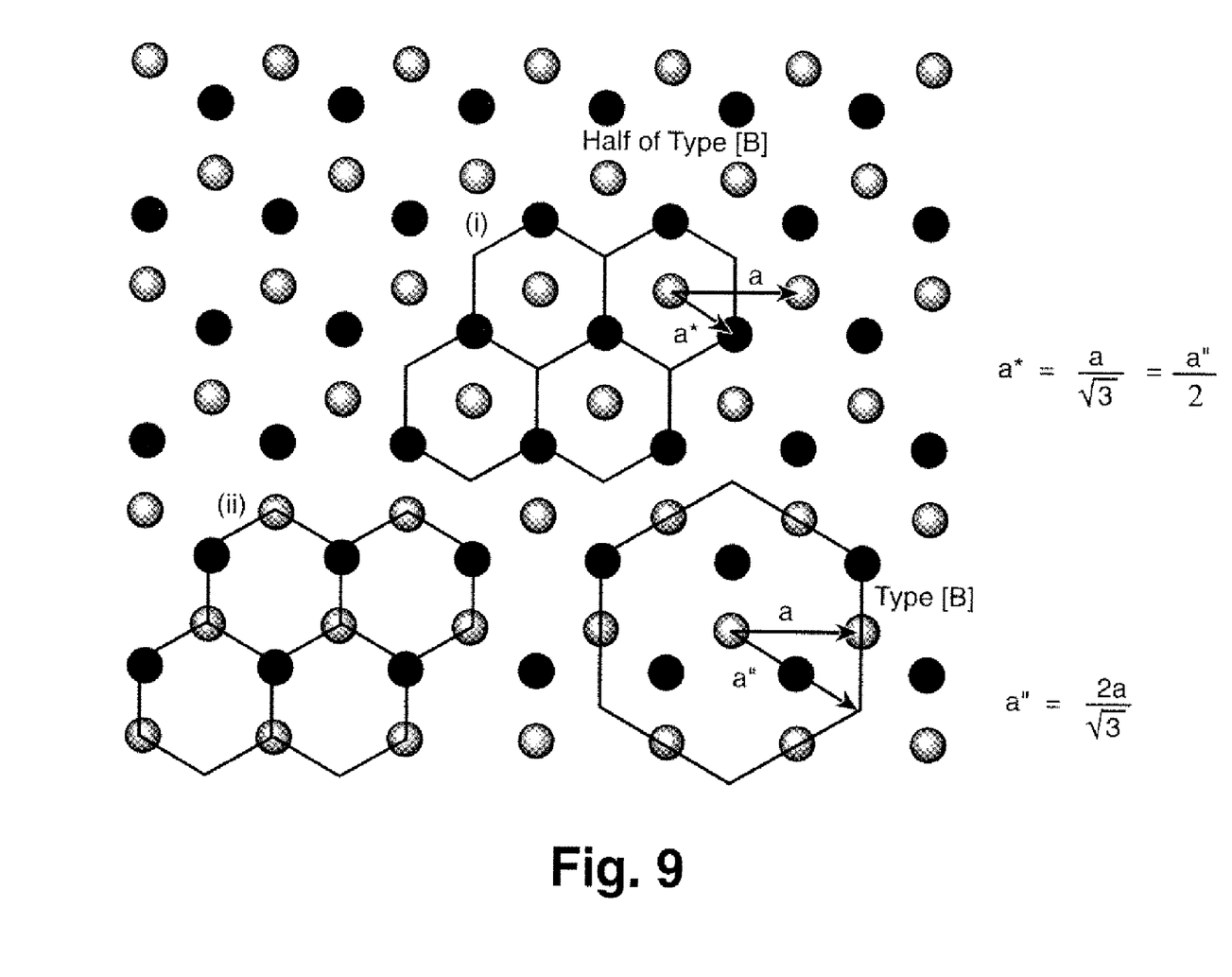
FIG. 9 shows fractional "½ of Type [B] alignment."

In addition, comparable alignments are possible with similar orientations, where the rhombohedral structures are smaller in relation to the underlying trigonal/hexagonal structure than in the cases of the Type [A] and [B] alignments discussed above. This is shown in FIGS. 8 and 9. The additional lattice-matching conditions for these possible arrangements must be considered as well.

In this reduced form of Type [A] alignment, if the rhombohedral dimensions are reduced relative to the underlying trigonal/hexagonal dimensions, there is a third lattice-matching condition as shown in FIG. 8, in which the coincidence lattice constant, a# (reflecting coincidence with the inner vertices of the underlying trigonal/hexagonal lattice), is ⅔ of the trigonal/hexagonal lattice constant a. We refer to this type of alignment as "⅔ of Type [A]" alignment.

Similarly, in the reduced form of Type [B] alignment, if the rhombohedral dimensions are reduced relative to the underlying trigonal/hexagonal dimensions, there is a fourth lattice-matching condition as shown in FIG. 9, in which the coincidence lattice constant, a" (reflecting coincidence with the inner vertices of the underlying trigonal/hexagonal lattice), is 2/√3 times the trigonal/hexagonal lattice constant a. We refer to this type of alignment as "½ of Type [B]" alignment With these four alignments and lattice matching conditions, a very widely applicable technology for lattice matched rhombohedral growth of group IV alloys has been developed, as well as group III-V and II-VI crystalline materials in zinc-blende structure, on trigonal or hexagonal substrates. The detailed technology is described below for Type [A], Type [B], ⅔ of Type [A] and ½ of Type [B].

Lattice Matched Rhombohedral Growth of Cubic Crystalline Alloys on Trigonal or Hexagonal Substrates

[1] Properties of Pseudo Alloys in Cubic Crystalline Structure

In the first order approximation where the material property of alloy changes linearly with composition, the lattice constant L of an alloy is determined by:

$$L(A_xB_{1-x}) = L_A + (1-x)L_B \text{ for binary compounds, } A_xB_{1-x} \quad (3)$$

$$L(A_xB_yC_{1-x-y}) = xL_A + yL_B + (1-x-y)L_C \text{ for ternary compounds, } A_xB_yC_{1-x-y} \quad (4)$$

$$L(A_xB_yC_zD_{1-x-y-z}) = xL_A + yL_B + zL_C + (1-x-y-z)L_D \text{ for quaternary compounds, } A_xB_yC_zD_{1-x-y-z} \quad (5)$$

When the alloy has a non-linear second-order term due to the mixing entropy, the lattice constant of binary alloy can be given by:

$$L(x) = A + Bx + Cx^2 \quad (6)$$

where C is called the Bowing Parameter and is four times the deviation of L(x) from linearity at x=0.5.

Similar mathematical relations can be made for non-linear properties, such as direct-indirect band-gap transition of binary, ternary, and quaternary alloys as well.

In many cases, the lattice constants of most of the group IV alloys (as well as group III-V and II-VI crystalline materials in zinc-blende structure) can be approximated with simplest linear approximation without using Bowing parameters, because the Bowing parameters of lattice-constants are usually small. On the other hand, the Bowing parameters for band-gap energy are significant and cannot be ignored.

For group IV elements with diamond structures, the lattice constants are given as: $L_C$(Carbon) 3.57 Å, $L_{Si}$ (Silicon)=5.43 Å, $L_{Ge}$ (Germanium) 5.66 Å and $L_{Sn}$ (Grey Tin diamond structure)=6.48 Å. For example, the lattice constant of $Si_{0.2}Ge_{0.3}C_{0.1}Sn_{0.4}$ can be calculated to be $0.2 \times L_{Si} + 0.3 \times L_{Ge} + 0.1 \times L_C + 0.4 \times L_{Sn} = 5.73$ Å.

Based on the foregoing, it is possible to change the lattice constant of a pseudo-alloy to a desired value in order to match it to the corresponding atomic distance of the substrate. However, a few percent change in the lattice constant may be equivalent to extremely high pressure in the alloy layer. Therefore, an unmatched alloy layer is prone to develop crystalline defects, such as serious threading dislocations that can destroy electronic devices.

For binary alloys, lattice-constant matching in accordance with the above equations can occur at or about only one alloy-composition since it has only one variable (x). On the other hand, ternary alloys have two variables (x and y) and quaternary alloys have three variables (x, y, and z). Therefore, lattice matching can occur at or about different compositions while varying multiple variables. This additional degree of freedom can control additional physical properties, such as band-gap energy and thermal expansion while the alloy is still in the lattice-matching condition. The following equations show the method to fix the composition to match multiple physical properties, such as index of refraction, band-gap energy, lattice constant, absorption coefficient, work-function, and so on.

Three properties will now be considered. L is a lattice constant, E is band-gap energy, $\alpha$ is a linear thermal expansion coefficient.

(1) For Binary Alloy ($A_xB_{1-x}$):

$$x \times L_A + (1-x) \times L_B = L_{Target}: \text{Matching the lattice constant} \quad (7)$$

(2) For Ternary Alloy ($A_xB_yC_{1-x-y}$):

$$x \times L_A + y \times L_B + (1-x-y) \times L_C = L_{Target}: \text{Matching the lattice constant} \quad (8)$$

$$x \times E_A + y \times E_B + (1-x-y) \times E_C = E_{Target}: \text{Matching the band-gap energy} \quad (9)$$

Two equations with two variables give one answer with unique x and unique y. Only the answer with x and y between 0 and 1 is meaningful. This answer matches two physical parameters at the same time.

(3) For Quaternary Alloy $A_xB_yC_zD_{1-x-y-z}$:

$$x \times L_A + y \times L_B + z \times L_C + (1-x-y-z) \times L_D = L_{Target}: \text{Matching the lattice constant,} \quad (10)$$

$$x \times E_A + y \times E_B + z \times E_C + (1-x-y-z) \times E_D = E_{Target}: \text{Matching the band-gap energy, and} \quad (11)$$

$$x + \alpha_A + y \times \alpha_B + z \times \alpha_C + (1-x-y-z) \times \alpha_D = \alpha_{Target}: \text{Matching the linear thermal expansion coefficient.} \quad (12)$$

Three equations with three variables give one answer with unique x, unique y, and unique z. Only the answer with x, y, and z between 0 and 1 is meaningful. This answer matches three physical parameters at the same time.

Lattice Matching Technique

As noted above, previous attempts were made to match the lattice constant of cubic structures directly by an approach wherein $L_{target} = L_{substrate}$ (the lattice constant of cubic substrate). In the present approach, $L_{target}$ should aim to match a corresponding atomic distance of a trigonal/hexagonal substrate, not the direct lattice constant of a cubic substrate. To do this, equation (14) below for type [A] alignment and equation (16) below for type [B] alignment are used. The following is the derivation of these equations.

For example, in the type [A] alignment, the following equation holds as shown in FIG. 2.

$$a'_{[2\overline{2}0]} = \frac{\sqrt{3}}{2} L_{target} = a_{Tri/Hex} \quad (13)$$

where a' is the atomic distance of [2-20] direction in FIG. 2 and $a_{Trig/Hex}$ is the lattice constant of basal plane of the trigonal or hexagonal crystalline substrate.

Therefore, $L_{target}$ should equal the transformed atomic distance, such as:

$$L_{target} = \frac{2}{\sqrt{3}} a_{Tri/Hex} \text{ for Type } [A] \text{ alignment} \quad (14)$$

As another example, in the type [B] alignment, the following equation holds as shown in FIG. 4.

$$a'_{[2\overline{2}0]} = \frac{\sqrt{3}}{2} L_{target} = a''_{Tri/Hex} = \frac{2}{\sqrt{3}} a_{Tri/Hex} \quad (15)$$

where a' is the atomic distance of [2-20] direction in FIG. 2, $a_{Trig/Hex}$ is the lattice constant of basal plane of the trigonal or hexagonal crystalline substrate and $a''_{Trig/Hex}$ is the transformed atomic distance that is aligned to a'.

Therefore, $L_{target}$ should equal the transformed atomic distance, such as:

$$L_{target} = \frac{4}{3} a_{Tri/Hex} \text{ for Type } [B] \text{ alignment} \quad (16)$$

As noted above, two other fractional coincidence atomic alignments are possible as shown in FIGS. 8 and 9, i.e., "Two Thirds (⅔) of Type-A" and "Half (½) of Type-B".

For ⅔ of Type [A] alignment as shown in FIG. 8, the following equation holds:

$$a'_{[2\overline{2}0]} = \frac{\sqrt{3}}{2} L_{target} = a''_{Tri/Hex} = \frac{2}{3} a_{Tri/Hex} \quad (17)$$

where a' is the atomic distance of [2-20] direction in FIG. 2 and $a\#_{Trig/Hex} = \frac{2}{3} \cdot a_{Trig/Hex}$ for "⅔ of Type-A" matching and $a_{Trig/Hex}$ is the lattice constant of basal plane of the trigonal or hexagonal crystalline substrate.

Therefore, $L_{target}$ should equal the transformed atomic distance, such as:

$$L_{target} = \frac{4}{3\sqrt{3}} a_{Tri/Hex} \text{ for "2/3 of Type } [A]\text{" alignment} \quad (18)$$

For the "half of type [B]" alignment, the following equation holds, as shown in FIG. 4:

$$a'_{[2\overline{2}0]} = \frac{\sqrt{3}}{2} L_{target} = \frac{1}{2} a''_{Tri/Hex} = \frac{1}{\sqrt{3}} a_{Tri/Hex} \quad (19)$$

where a' is the atomic distance of [2-20] direction in FIG. 2, $a_{Trig/Hex}$ is the lattice constant of basal plane of the trigonal or hexagonal crystalline substrate and $$\frac{1}{2} a''_{Tri/Hex}$$

is the transformed atomic distance that is aligned to a'.

Therefore, $L_{target}$ should equal the transformed atomic distance, such as:

$$L_{target} = \frac{2}{3} a_{Tri/Hex} \text{ for "1/2 of Type [B]" alignment} \quad (20)$$

There are many crystal wafers that have a trigonal crystal structure. The following list shows a few selected materials with their lattice constants, $a_{Tri}$ and $a_{Hex}$, as the lattice constants of basal plane and c as vertical lattice constant.
Trigonal Crystals (by Point Group Symmetry):
Sapphire ($Al_2O_3$), $a_{Tri}$=4.758 Å, c=12.99 Å
Gallium Nitride (GaN), $a_{Tri}$=3.189 Å, c=5.185 Å
Aluminum Nitride (AlN), $a_{Tri}$=3.11 Å, c=4.98 Å
Indium Nitride (InN), $a_{Tri}$=3.54 Å, c=8.70 Å
Zinc Oxide (ZnO), $a_{Tri}$=3.25 Å, c=5.21 Å
Lithium Niobate ($LiNbO_3$), $a_{Tri}$=5.148 Å, c=13.863 Å
Lithium Copper Tantalate (LiCuTaO3, Li=0.667, Cu=0.333) $a_{Tri}$=5.2004 Å, c=13.788 Å
Lithium Tantalum Nitride Oxide(LTNO) (Li16N8O1Ta2), $a_{Tri}$=5.983 Å, c=9.168 Å
(In this list, trigonal lattice was described in the hexagonal frame instead of the rhombohedral frame.)
Hexagonal Crystals (by Point Group Symmetry):
Quartz, $a_{Hex}$=4.91 Å, c=5.40 Å
Boron Nitride (BN) in Hexagonal form, (Space group $D_{6C}$-$P6_3mmc$), $a_{Hex}$=2.50 Å, c=6.66 Å

Therefore, the equations (14), (16), (18) and (20) can be applied to all trigonal crystal and hexagonal crystal wafers made with the materials, including but not limited to the above list. The use of these equations is not limited to group IV alloys in diamond structure. They may also be applied to group III-V and II-VI materials in zinc-blende structure. The above lattice matching equations (14), (16), (18), and (20) apply for all of these materials. The trigonal and hexagonal crystals can both be described in hexagonal frame, but the main difference between the two structures is that the hexagonal crystal allows 60° rotational symmetry, whereas the trigonal crystal has only 120° rotational symmetry without 60° rotational symmetry.

With this general expansion of technology, we formulate a group IV alloy made with any of Si, Ge, C, and Sn, or group II-V and II-VI materials in zinc-blende structure, on any of the trigonal or hexagonal substrates, whose alloy composition is designed to hold the equation (14) in Type [A] alignment, equation (16) in Type [B] alignment, (18) in ⅔ of Type [A] alignment, or equation (20) in half of Type [B] alignment within ±10% error of alloy composition. We also note that the same analysis should be applicable to other materials in Body Centered Cubic (BCC) and Face Centered Cubic (FCC) structures as well.

For example, $Si_{0.14}Sn_{0.86}$ can match lattice constant of sapphire in Type [B] alignment. Therefore the alloy of $Si_xSn_y$ on sapphire in the range of y=0.86±0.086(10%)= 0.774~0.946 and x=1−y=0.226~0.054 is within this formulation.
General XRD Method for Cubic Crystalline Material on any Trigonal/Hexagonal Substrate
(1) Bragg Angle of X-Ray Diffraction Peak:
Generally, X-ray diffraction occurs whenever the Bragg condition is satisfied:

$$2d^* \cdot \sin\theta = n \cdot \lambda \quad (b\,21)$$

where d is the atomic spacing distance of plane (h,k,l), θ is the X-ray diffraction angle, λ is the wavelength of the X-ray, and n is an integer. Here d(h,k,l) is determined by the crystal structure and the lattice constant, L.

In cubic diamond structure, $$d_{h,k,l} = \frac{L}{\sqrt{h^2 + k^2 + l^2}}. \quad (22)$$

$L_{alloy}(x,y,z)$ is defined to represent the lattice constant of a pseudo-alloy such as L $(A_xB_{1-x})$ $L(A_xB_yC_{1-x-y})$ and $L(A_xB_yC_zD_{1-x-y-z})$, as shown in the previous equation (3), (4), and (5). Then, $$d_{h,k,l}(x, y, z) = \frac{L_{alloy}(x, y, z)}{\sqrt{h^2 + k^2 + l^2}}. \quad (23)$$

Therefore, the XRD peak occurs at the angle $\theta_{h,k,l}(x,y,z)$, such that:

$$\sin\theta_{h,k,l}(x+y+z) = \frac{n \cdot \lambda}{2 \cdot d_{h,k,l}(x, y, z)} = \frac{\pi \cdot \lambda \cdot \sqrt{h^2 + k^2 + l^2}}{2 \cdot L_{alloy}(x, y, z)}. \quad (24)$$

(2) Inter-Planar Angle:
For a cubic diamond structure, the inter-planar angle cubic, $\phi_{cubic}$, between two planes, $(h_1, k_1, l_1)$ and $(h_2, k_2, l_2)$, is given by:

$$\cos\phi_{cubic} = \frac{h_1 h_2 + k_1 k_2 + l_1 l_2}{\sqrt{(h_1^2 + k_1^2 + l_1^2) \cdot (h_2^2 + k_2^2 + l_2^2)}}. \quad (25)$$

(For general X-ray diffraction analysis, refer to *Elements of X-ray Diffraction* by B. D. Cullity, Addison-Wesley Publishing Co., $2^{nd}$ or higher edition.)

Similarly, for a trigonal crystal in hexagonal frame and a hexagonal crystal, the inter-planar angle, $\phi_{Tri/Hex}$, between two planes, $(h_1, k_1, l_1)$ and $(h_2, k_2, l_2)$, is given by:

$$\cos\phi_{Tri/Hex} = \frac{h_1 h_2 + k_1 k_2 + \frac{1}{2}(h_1 k_2 + k_1 h_2) + \frac{3a^2}{4c^2} l_1 l_2}{\sqrt{\left(h_1^2 + k_1^2 + h_1 k_1 + \frac{3a^2}{4c^2} l_1^2\right) \cdot \left(h_2^2 + k_2^2 + h_2 k_2 + \frac{3a^2}{4c^2} l_2^2\right)}}. \quad (26)$$

(3) Twin Detection XRD for Cubic Crystalline Alloys on Trigonal/Hexagonal Substrate:

Using the above equations (24), (25), and (26), the twin detection XRD method can be completed for all general cubic crystalline alloys on any trigonal or hexagonal substrate.

As an example, calculated XRD peak positions for selected cubic crystalline alloy compositions on selected substrates are shown in the following tables. The actual compositions are not limited to these tables, but can be extended according to the equations from (3) to (20).

TABLE 1

Selected list of cubic crystalline alloy compositions on various substrates in the lattice-match condition in Type A and Type B.

| Si Ge C Sn Alloy/Substrate-Type (A or B) | \multicolumn{4}{c}{Epitaxial Layer} | Lattice C- of pseudo alloy | Substrate Name Type A | Lattice C. Type B |
|---|---|---|---|---|---|---|---|
| | 5.431 | 5.658 | 3.57 | 6.489 | | | |
| | \multicolumn{4}{c}{Alloy Composition} | | | |
| Sapphire Substrate | | | | | | | |
| SiGe/Sapphire-A | 0.72 | 0.28 | | | 5.49 | | |
| SiSn/Sapphire-B | 0.14 | | | 0.86 | 6.34 | Sapphire | 4.758 |
| GeSn/Sapphire-B | | 0.18 | | 0.82 | 6.34 | 5.49 | 6.34 |
| CSn/Sapphire-B | | | 0.05 | 0.95 | 6.34 | | |
| SiGeCSn/Sapphire-B | 0.03 | 0.11 | 0.01 | 0.85 | 6.34 | | |
| GaN Substrate | | | | | | | |
| SiC/GaN-A | 0.06 | | 0.94 | | 3.68 | | |
| GeC/GaN-A | | 0.055 | 0.945 | | 3.68 | GaN | 3.189 |
| SiC/GaN-B | 0.365 | | 0.635 | | 4.25 | 3.68 | 4.25 |
| GeC/GaN-B | | 0.325 | 0.675 | | 4.25 | | |
| SnC/GaN-B | | | 0.768 | 0.232 | 4.25 | | |
| SiGeCSn/GaN-B | 0.11 | 0.09 | 0.7 | 0.1 | 4.25 | | |
| AlN/Substrate | | | | | | | |
| SiC/AlN-A | 0.01 | | 0.99 | | 3.59 | | |
| SiC/AlN-B | 0.31 | | 0.69 | | 4.15 | AlN | 3.11 |
| GeC/AlN-B | | 0.28 | 0.72 | | 4.15 | 3.59 | 4.15 |
| CSn/AlN-B | | | 0.8 | 0.2 | 4.15 | | |
| SiGeC/AlN-B | 0.2 | 0.1 | 0.7 | | 4.15 | | |
| SiGeCSn/AlN-B | 0.05 | 0.05 | 0.77 | 0.13 | 4.15 | | |
| InN Substrate | | | | | | | |
| SiC/InN-A | 0.28 | | 0.72 | | 4.09 | | |
| GeC/InN-A | | 0.25 | 0.75 | | 4.09 | InN | 3.54 |
| CSn/InN-A | | | 0.822 | 0.178 | 4.09 | 4.09 | 4.72 |
| SiGeCSn/InN-A | 0.05 | 0.05 | 0.79 | 0.11 | 4.09 | | |
| SiC/InN-B | 0.62 | | 0.38 | | 4.72 | | |
| GeC/InN-B | | 0.55 | 0.45 | | 4.72 | | |
| CSn/InN-B | | | 0.605 | 0.395 | 4.72 | | |
| SiGeCSn/InN-B | 0.25 | 0.05 | 0.5 | 0.2 | 4.72 | | |
| ZnO Substrate | | | | | | | |
| SiC/ZnO-A | 0.095 | | 0.905 | | 3.75 | | |
| GeC/ZnO-A | | 0.084 | 0.916 | | 3.75 | ZnO | 3.25 |
| SiC/ZnO-B | 0.41 | | 0.59 | | 4.33 | 3.75 | 4.33 |
| CSn/ZnO-B | | | 0.74 | 0.26 | 4.33 | | |
| SiGeCSn/ZnO-B | 0.195 | 0.05 | 0.655 | 0.1 | 4.33 | | |
| Quartz Substrate | | | | | | | |
| Ge(Sn)/Quartz-A | | 0.99 | | 0.01 | 5.67 | | |
| SiSn/Quartz-A | 0.77 | | | 0.23 | 5.67 | Quartz | 4.91 |
| CSn/Quartz-A | | | 0.28 | 0.72 | 5.67 | 5.67 | 6.55 |
| SiGeCSn/Quartz-A | 0.2 | 0.2 | 0.15 | 0.45 | 5.67 | | |

TABLE 2

Selected list of cubic crystalline alloy compositions on various substrates in the fractional lattice-match condition in ⅔ of type A and ½ of type B.

| Si Ge C Sn Alloy/Substrate-Type | \multicolumn{4}{c}{Epitaxial Layer} | Lattice C. of pseudo alloy | Substrate Name ⅔ of Type A | Lattice C. ½ of Type B |
|---|---|---|---|---|---|---|---|
| | 5.431 | 5.658 | 3.57 | 6.489 | | | |
| | \multicolumn{4}{c}{Alloy Composition} | | | |
| Sapphire Substrate | | | | | | | |
| SiC/Sapphire-⅔ of A | 0.05 | | 0.95 | | 3.66 | Sapphire | 4.758 |
| GeC/Sapphire-⅔ of A | | 0.045 | 0.955 | | 3.66 | 3.66 | 3.17 |
| Lithium Niobate (LiNbO3) Substrate | | | | | | | |
| SiC/LiNbO3-⅔ of A | 0.21 | | 0.79 | | 3.96 | LiNbO3 | 5.148 |
| GeC/LiNbO3-⅔ of A | | 0.185 | 0.815 | | 3.96 | 3.96 | 3.43 |
| Lithium Tantalum Nitride Oxide (LTNO) Substrate | | | | | | | |
| SiC/LTNO - ⅔ of A | 0.555 | | 0.445 | | 4.60 | Li16N8O1Ta2 | 5.982 |
| SiC/LTNO - ½ of B | 0.225 | | 0.775 | | 3.99 | 4.60 | 3.99 |

TABLE 2-continued

Selected list of cubic crystalline alloy compositions on various substrates in the fractional lattice-match condition in ⅔ of type A and ½ of type B.

| | Epitaxial Layer | | | | | | |
|---|---|---|---|---|---|---|---|
| Si Alloy/Substrate-Type | Si | Ge | C | Sn | Lattice C. of | Substrate Name | Lattice C. |
| | 5.431 | 5.658 | 3.57 | 6.489 | pseudo alloy | ⅔ of Type A | ½ of Type B |
| | Alloy Composition | | | | | | |
| GeC/LTHO - ½ of B | | 0.2 | 0.8 | | 3.99 | | |
| SiGeC/LTNO - ½ of B | 0.1 | 0.11 | 0.79 | | 3.99 | | |
| LiCuTaO3 Substrate (Li = 0.667, Cu = 0.333) | | | | | | | |
| SiC/LiCuO3 - ⅔ of A | 0.23 | | 0.77 | | 4.00 | LiCuTaO3 | 5.2004 |
| GeC/LiCuO3 - ⅔ of A | | 0.205 | 0.795 | | 4.00 | 4.00 | 3.47 |

The Bragg angles of X-ray diffraction were calculated and are listed in the following tables for select lattice matching conditions on various substrates. Table 3 and Table 5 were calculated with copper Cu K-$\alpha_1$ X-ray source and Table 4 and Table 6 were calculated with X-ray from cobalt, with weighted average of Co K-$\alpha_1$ and K-$\alpha_2$.

TABLE 3

Bragg angles (°) for selected XRD peaks of lattice matched alloy on various substrates (X-ray source: Cu K-$\alpha_1$).
Cu K-a1
X-ray Wavelength: 1.54056 Angstrom

| | L.C. of alloy | 1st order Bragg angle, Theta, for various peaks (in degrees) | | | | |
|---|---|---|---|---|---|---|
| | | {111} | {220} | {113} | {224} | {004} |
| Sapphire Type A | 5.49 | 14.065 | 23.381 | 27.732 | 43.421 | 34.140 |
| Sapphire Type B | 6.34 | 12.148 | 20.099 | 23.763 | 36.527 | 29.077 |
| GaN Type A | 3.68 | 21.257 | 36.301 | 43.965 | N/A | 56.852 |
| GaN Type B | 4.25 | 18.296 | 30.839 | 36.950 | 62.611 | 46.466 |
| AlN Type A | 3.59 | 21.816 | 37.364 | 45.367 | N/A | 59.121 |
| AlN Type A | 4.15 | 18.753 | 31.667 | 37.995 | 65.408 | 47.940 |
| InN Type A | 4.09 | 19.038 | 32.187 | 38.655 | 67.315 | 48.880 |
| InN Type B | 4.72 | 16.419 | 27.489 | 32.769 | 53.081 | 40.752 |
| ZnO Type A | 3.75 | 20.841 | 35.520 | 42.942 | N/A | 55.248 |
| ZnO Type B | 4.33 | 17.946 | 30.209 | 36.157 | 60.633 | 45.363 |
| Quartz Type A | 5.67 | 13.609 | 22.597 | 26.780 | 41.723 | 32.916 |

TABLE 4

Bragg angles (°) for selected XRD peaks of lattice matched alloy on various substrates (X-ray source: Co K-$\alpha$ [weighted average]).
Co K-a (average)
X-ray Wavelength: 1.79026 Angstrom

| | L C_alloy | 1st order Bragg angle, Theta, for various peaks (in degrees) | | | | |
|---|---|---|---|---|---|---|
| | | {111} | {220} | {113} | {224} | {004} |
| Sapphire Type A | 5.49 | 16.404 | 27.462 | 32.736 | 53.012 | 40.707 |
| Sapphire Type B | 6.34 | 14.155 | 23.537 | 27.922 | 43.763 | 34.385 |
| GaN Type A | 3.68 | 24.917 | 43.471 | 53.779 | N/A | 76.647 |
| GaN Type B | 4.25 | 21.395 | 36.564 | 44.310 | N/A | 57.402 |
| AlN Type A | 3.59 | 25.586 | 44.849 | 55.788 | N/A | 85.835 |
| AlN Type A | 4.15 | 21.937 | 37.595 | 45.674 | N/A | 59.630 |
| InN Type A | 4.09 | 22.276 | 38.245 | 46.541 | N/A | 61.096 |

TABLE 4-continued

Bragg angles (°) for selected XRD peaks of lattice matched alloy on various substrates (X-ray source: Co K-$\alpha$ [weighted average]).
Co K-a (average)
X-ray Wavelength: 1.79026 Angstrom

| | L C_alloy | 1st order Bragg angle, Theta, for various peaks (in degrees) | | | | |
|---|---|---|---|---|---|---|
| | | {111} | {220} | {113} | {224} | {004} |
| InN Type B | 4.72 | 19.176 | 32.439 | 38.975 | 68.291 | 49.340 |
| ZnO Type A | 3.75 | 24.421 | 42.466 | 52.343 | N/A | 72.709 |
| ZnO Type B | 4.33 | 20.981 | 35.783 | 43.286 | N/A | 55.783 |
| Quartz Type A | 5.67 | 15.869 | 26.521 | 31.574 | 50.661 | 39.160 |

TABLE 5

Bragg angles (°) for selected XRD peaks of alloys of fractional lattice matching condition on various substrates (X-ray source: Cu K-$\alpha_1$).

| | L.C._alloy | 1st order Bragg angle, Theta, for various peaks (in degree) | | | | |
|---|---|---|---|---|---|---|
| | | {111} | {220} | {113} | {224} | {004} |
| Sapphire - ⅔ of Type A | 3.66 | 21.378 | 36.532 | 44.268 | N/A | 57.335 |
| Sapphire - ½ of Type B | 3.17 | 24.890 | 43.415 | 53.698 | N/A | 76.400 |
| LiNbO3 - ⅔ of Type A | 3.96 | 19.689 | 33.379 | 40.176 | N/A | 51.083 |
| LiNbO3 - ½ of Type B | 3.43 | 22.890 | 39.434 | 48.144 | N/A | 63.934 |
| LTNO - ⅔ of Type A | 4.6 | 16.860 | 28.270 | 33.737 | N/A | 42.052 |
| LTNO - ½ of Type B | 3.99 | 19.535 | 33.095 | 39.813 | 71.043 | 50.553 |
| LiCuTaO3 - ⅔ of Type A | 4.00 | 19.484 | 33.002 | 39.694 | 70.630 | 50.379 |
| LiCuTaO3 - ½ of Type B | 3.47 | 22.612 | 38.893 | 47.412 | N/A | 62.614 |

TABLE 6

Bragg angles (°) for selected XRD peaks of alloys of
fractional lattice matching condition on various substrates
(X-ray source: Co K-α [weighted average])

1st order Bragg angle, Theta, for various peaks (in degree)

| | L.C._alloy | {111} | {220} | {113} | {224} | {004} |
|---|---|---|---|---|---|---|
| Sapphire - ⅔ of Type A | 3.66 | 25.063 | 43.769 | 54.208 | N/A | 78.038 |
| Sapphire - ½ of Type B | 3.17 | 29.281 | 53.004 | 69.477 | N/A | N/A |
| LiNbO3 - ⅔ of Type A | 3.96 | 23.049 | 39.743 | 48.564 | N/A | 64.712 |
| LiNbO3 - ½ of Type B | 3.43 | 26.873 | 47.573 | 59.945 | N/A | N/A |
| LTNO - ⅔ of Type A | 4.6 | 19.697 | 33.394 | 40.195 | 72.423 | 51.112 |
| LTNO - ½ of Type B | 3.99 | 22.866 | 39.386 | 48.079 | N/A | 63.815 |
| LiCuTaO3 - ⅔ of Type A | 4 | 22.805 | 39.268 | 47.919 | N/A | 63.525 |
| LiCuTaO3 - ½ of Type B | 3.47 | 26.539 | 46.855 | 58.822 | N/A | N/A |

The inter-planar angle between {111} plane and a few other planes are listed in the following Table 7.

TABLE 7

Inter-planar angle between {111} plane and various other planes.

| Planes | Inter-Planar Angle (°) |
|---|---|
| {111}/{224} | 19.471 |
| {111}/{113} | 29.496 |
| {111}/{220} | 35.264 |
| {111}/{004} | 54.736 |

These calculated numbers can be applied to the technology of copending application Ser. No. 12/254,150, entitled "METHOD OF GENERATING X-RAY DIFFRACTION DATA FOR INTEGRAL DETECTION OF TWIN DEFECTS IN SUPER-HETERO-EPITAXIAL MATERIALS," and Ser. No. 12/288,380, entitled "X-RAY DIFFRACTION WAFER MAPPING METHOD FOR RHOMBOHEDRAL SUPER-HETERO-EPITAXY," which are both incorporated herein by reference in their entirety.

Therefore, the twin detection XRD can be expanded to all group IV alloys, as well as group III-V and group II-VI crystalline materials in zinc-blende structure on any trigonal or hexagonal substrate, with the Bragg angles that are calculated in Tables 2 and 3 according to equation (19) and the inter-planar angles that are calculated in the Table 4 according to the equation (20). With appropriate [h,j,k] values, the same techniques could also be applied to other BCC and FCC materials.

The equations and tabulated numbers above can be used to apply the methods of accompanying application Ser. No. 12/254,150, entitled "METHOD OF GENERATING X-RAY DIFFRACTION DATA FOR INTEGRAL DETECTION OF TWIN DEFECTS IN SUPER-HETERO-EPITAXIAL MATERIALS," and Ser. No. 12/288,380, entitled "X-RAY DIFFRACTION WAFER MAPPING METHOD FOR RHOMBOHEDRAL SUPER-HETERO-EPITAXY," which are both incorporated herein by reference in their entirety, for XRD twin detection to all group IV semiconductor alloys made from any of Si, Ge, C, and Sn elements, and group III-V and group II-VI crystalline materials in zinc-blende structure, on any trigonal/hexagonal substrate.

ADVANTAGES OF THE TECHNOLOGY

Figure 10:
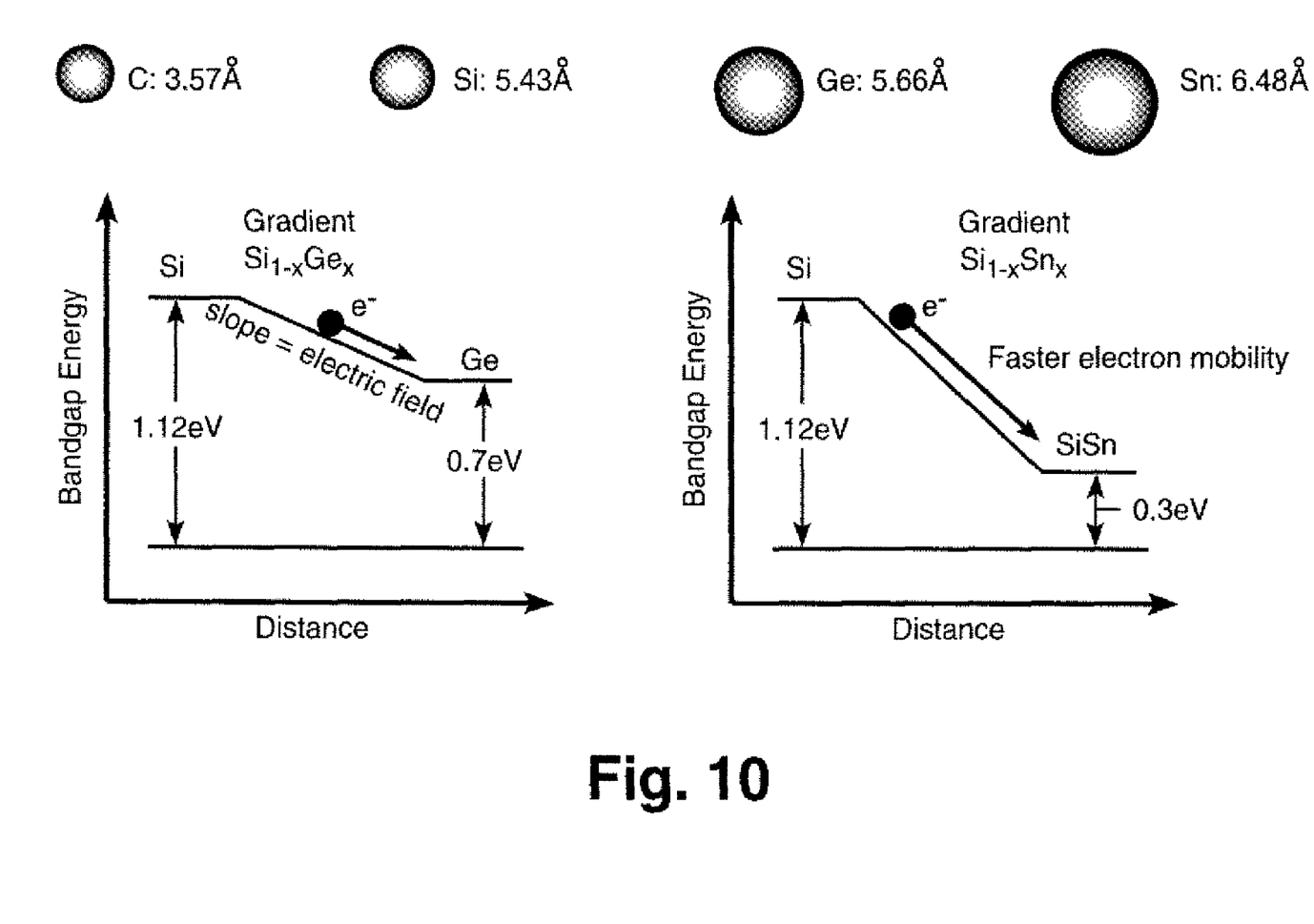
FIG. 10 illustrates (Top) lattice constants of group IV semiconductor elements, (Lower Left) fast electron mobility in SiGe HBT, and (Lower Right) even faster electron mobility in SiGeCSn HBT.

The rhombohedral-trigonal (hexagonal) lattice matching technology described herein enables the development of new cubic crystalline semiconductor alloys substantially relieved from misfit dislocation defects on various substrates. One example is shown in FIG. 10 for today's fastest transistor, Hetero Bipolar Transistor (HET), which is made with SiGe alloy with small Ge content. The electron mobility of the thin Base region of HBT is much faster than that of conventional Si transistors because the conduction band of the gradient SiGe alloy layer in the Base region has a built-in electric field due to the band-gap energy difference between the Si layer and the SiGe layer, which is shown as "Slope" in FIG. 10. In spite of these advantages, it has been extremely difficult to make a defect-free SiGe alloy with high Ge content because the lattice constant of Ge is larger than that of Si, as shown at the top of FIG. 10. This difference resulted in a critical thickness, which is a theoretical limit that epitaxial layer can be grown without dislocation defects.

The present invention makes it possible to incorporate high content of Ge and Tin (Sn) atoms into Si free from the prior critical thickness limit because it is lattice-matched, in order to increase the built-in electric field for even faster SiGeCSn HBT devices and more efficient SiGeCSn TE devices. Note the greater slope in the graph for SiGeCSn on the lower right-hand side of FIG. 10. Because faster mobility of electrons and holes are very important to increase ZT factor of TE materials, this technology will be of great use in developing faster semiconductors.

Thus, it is apparent that the methods and materials described in the present disclosure satisfy the objects of the invention set forth above.

The present invention is further discussed in Y. Park, G. C. King, S. H. Choi, Rhombohedral epitaxy of cubic SiGe on trigonal c-plane sapphire, Journal of Crystal Growth 310 (2008) 2724-2731, herein incorporated by reference in its entirety.

Although the present invention has been described in detail, it should be understood that various changes, substitutions, and alterations may be readily ascertainable by those skilled in the art and may be made herein without departing from the spirit and scope of the present invention as defined by the following claims.

What is claimed as new and desired to be secured by Letters Patent of the United States is:

1. A method of forming a hetero-epitaxial crystal structure of a group IV, group III-V or group II-VI alloy on the basal (0001) plane of a trigonal crystal or hexagonal crystal substrate so as to minimize crystalline dislocation defects between the hetero-epitaxial crystal structure of the group IV, group III-V or group II-VI alloy and the trigonal crystal or hexagonal crystal substrate, said method comprising:
   (a) if said alloy is a type in which the trigonal arrangement of atomic sites of the {111} plane of said alloy crystal directly meets the hexagonal or trigonal coincidence lattice of atomic sites in the basal plane of said substrate without any rotation, calculating a target lattice constant ($L_{target}$) as $2/\sqrt{3}$*basal plane lattice constant of the substrate ($a_{tri/hex}$);

(b) if said alloy is of a type in which the trigonal arrangement of atomics sites of the {111} plane of said alloy crystal meets the hexagonal or trigonal coincidence lattice of atomic sites in the basal plane of said substrate with a 30° rotation, calculating $L_{target}$ as 4/3*basal plane lattice constant of the substrate ($a_{tri/hex}$);

(c) if said alloy is of a type in which the trigonal arrangement of atomic sites of the {111} plane of said alloy crystal directly meets the inner vertices of the hexagonal or trigonal coincidence lattice of atomic sites in the basal plane of said substrate without any rotation, calculating a target lattice constant ($L_{target}$) as $4/(3*\sqrt{3})$*basal plane lattice constant of the substrate ($a_{tri/hex}$);

(d) if said alloy to be of a type in which the trigonal arrangement of atomic sites of the {111} plane of said alloy crystal meets the inner vertices of the hexagonal or trigonal coincidence lattice of atomic sites in the basal plane of said substrate with a 30° rotation, calculating $L_{target}$ as ⅔*basal plane lattice constant of the substrate ($a_{tri/hex}$);

(e) determining the respective proportions of the group IV, group III-V or group II-VI elements in said alloy by approximating $L_{target}$ as a linear function of the individual lattice constants for the constituent group IV, group III-V or group II-VI elements weighted in accordance with said proportions and a Bowing Parameter, and solving for said proportions; and (f) growing the group IV, group III-V or group II-VI alloy on the basal (0001) plane of the trigonal crystal or hexagonal crystal substrate in the determined respective proportions to thereby form the hetero-epitaxial crystal structure on the trigonal crystal or hexagonal crystal substrate so as to minimize crystalline dislocation defects between the hetero-epitaxial crystal structure of the group IV, group III-V or group II-VI alloy and the trigonal crystal or hexagonal crystal substrate.

2. The method of claim 1, wherein the Bowing Parameter is treated as zero, thereby reducing step c to the step of solving a system of linear equations.

3. The method of claim 2, wherein said alloy is a binary alloy in which the two group IV, group III-V or group II-VI components have relative proportions of x and 1−x and lattice constant $L_A$ and $L_B$, and, after $L_{target}$ has been determined in accordance with steps (a) or (b) in claim 1, x is determined by solving the equation $x*L_A+(1-x)*L_B=L_{target}$.

4. The method of claim 2, wherein said alloy is a ternary alloy in which the three group IV, group III-V or group II-VI components have relative proportions of x, y and 1−x−y, lattice constants $L_A$, $L_B$ and $L_C$, and band-gap energies $E_A$, $E_B$ and $E_C$, and, after $L_{target}$ has been determined in accordance with steps (a) or (b) in claim 1, x and y are determined by solving the equations $x*L_A+y*L_B+(1-x-y)*L_C=L_{target}$ and $x*E_A+y*E_B+(1-x-y)*E_C=E_{target}$ and the solution is chosen for which x and y are each between 0 and 1.

5. The method of claim 2, wherein said alloy is a quaternary alloy in which the four group IV, Group III-V or group II-VI components have relative proportions of x, y, z and 1−x−y−z, lattice constants $L_A$, $L_B$, $L_c$ and $L_D$, band-gap energies $E_A$, $E_B$, $E_C$ and $E_D$, and linear thermal expansion coefficients $\alpha_A$, $\alpha_B$, $\alpha_C$, and $\alpha_D$, and, after $L_{target}$ has been determined in accordance with steps (a) or (b) in claim 1, x, y and z are determined by solving the equations $x*L_A+y*L_B+z*L_c+(1-x-y-z)*L_D=L_{target}$, $x*E_A+y*E_B+z*E_C+(1-x-y-z)*E_D=E_{target}$, and $x*\alpha_A+y*\alpha_B+z*\alpha_C+(1-x-y-z)*\alpha_D=\alpha_{target}$, and the solution is chosen for which x, y and z are each between 0 and 1.

* * * * *